United States Patent [19]

Lee

[11] 4,232,115
[45] Nov. 4, 1980

[54] BLEACHABLE PHOTOGRAPHIC SENSITIZING DYES

[75] Inventor: Ross A. Lee, Webster, N.Y.

[73] Assignee: E. I. Du Pont de Nemours and Company, Wilmington, Del.

[21] Appl. No.: 15,005

[22] Filed: Feb. 22, 1979

Related U.S. Application Data

[63] Continuation-in-part of Ser. No. 890,788, Mar. 27, 1978, abandoned.

[51] Int. Cl.$^3$ .................. C07D 327/06; C07D 411/06; C07D 405/14
[52] U.S. Cl. .................................... 430/522; 542/432; 542/441; 430/592; 430/595
[58] Field of Search .................. 96/140, 139, 129, 130; 542/441, 432; 260/327 S

[56] References Cited

U.S. PATENT DOCUMENTS

| | | | |
|---|---|---|---|
| 2,748,114 | 5/1956 | Brooker | 542/441 |
| 2,882,159 | 4/1959 | Brooker et al. | 96/102 |
| 3,148,065 | 9/1964 | Craig et al. | 96/139 |
| 3,395,017 | 7/1968 | Knott | 96/84 |
| 3,598,813 | 8/1971 | Knott | 542/441 |
| 3,682,899 | 8/1972 | Nishio | 542/441 |
| 3,764,322 | 10/1973 | Kampfer | 96/29 D |

OTHER PUBLICATIONS

Barbieri et al., Tet. Letter, 1971, #52, pp. 4913–4914.

*Primary Examiner*—Arthur P. Demers

[57] ABSTRACT

A novel group of photographic sensitizing dyes is prepared by reacting the 5,7-dimethyl-1,2-benzoxathian-4-one-2,2-dioxide sultone nucleus with other organic compounds capable of forming merocyanine, oxonol or styryl dyes therewith. The resulting dyes are particularly useful in the sensitization of silver halide emulsions and provide excellent speed and low after-processing dye stain.

10 Claims, No Drawings

BLEACHABLE PHOTOGRAPHIC SENSITIZING DYES

RELATION TO OTHER CASES

This is a continuation-in-part of Ser. No. 890,788 filed Mar. 27, 1978, now abandoned.

DESCRIPTION

1. Technical Field

This invention relates generally to photographic sensitizing dyes, and specifically to sensitizing dyes useful in silver halide emulsions, to methods for preparing such dyes, and to photographic silver halide emulsions containing these new dyes.

2. Background Art

It is known in the art that a number of photographic sensitizing dyes can be used to extend the spectral region of photosensitive silver halide emulsions, but very few of them produce good photographic speed and can be bleached with hydroxide ion, a common constituent of the fluid or fluids used to process imagewise-exposed film. The present invention provides a class of sensitizing dyes which possess these properties.

DISCLOSURE OF INVENTION

This invention is directed to a novel class of dyes which function as optical sensitizers or as bleachable filter dyes for silver halide emulsions, the dye having one of the following formulae: formulae:

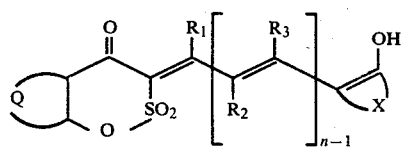

(A)

wherein Q represents sufficient carbon atoms to complete a benzo or naptho nucleus, or a substituted benzene or napthalene nucleus, $R_1$, $R_2$ and $R_3$ each represent H or a $C_1$-$C_3$ alkyl group, n=1, 2 or 3, and X represents sufficient nonmetallic atoms to complete a 5- or 6-membered heterocyclic or carbocyclic nucleus;

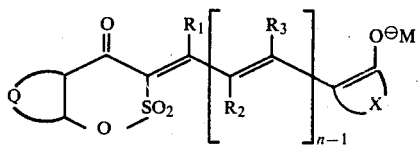

(B)

wherein Q, $R_1$, $R_2$, $R_3$ and n are the same as in formula A, and M is a mono-, di-, or trivalent metal;

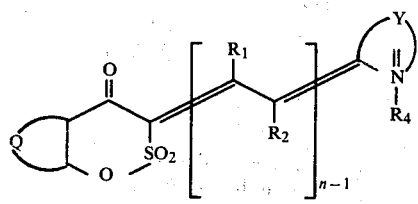

(C)

wherein Q, $R_1$, $R_2$ and n are the same as in formula A, $R_4$ is a $C_1$-$C_{12}$ alkyl, and Y represents sufficient nonmetallic atom to complete a 5- or 6-membered heterocyclic nucleus;

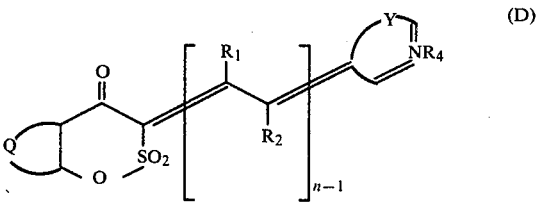

(D)

wherein Q, $R_1$, $R_2$, n, $R_4$, and Y are the same as in formula C; and

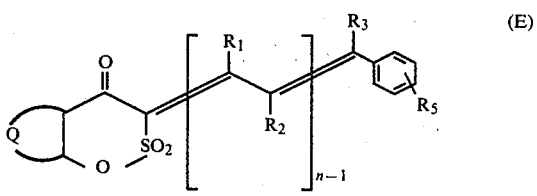

(E)

wherein Q, $R_1$, $R_2$, $R_3$ and n are the same as in formula A and $R_5$ can be H, a $C_1$-$C_{12}$ alkyl group, an $NO_2$ group, an alkyloxy or alkylthio group wherein the alkyl group contains 1-6 carbon atoms, or a dialkylamino group wherein each alkyl group contains 1-6 carbon atoms.

To synthesize these dyes an organic sultone, 5,7-dimethyl-1,2-benzoxathian-4-one-2,2-dioxide (I)

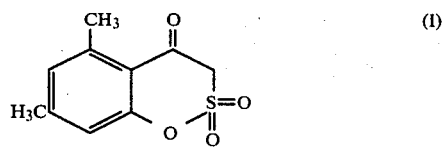

(I)

is condensed with a common dye intermediate reaction material to form suitable merocyanine, merocarbocyanine, oxonol, or styryl dyes of the general formulas set forth above.

Silver halide emulsions containing these dyes have excellent photographic speed and low afterprocessing dye stain. This is surprising since other starting nuclei with structures similar to (I) do not produce satisfactory sensitizing dyes.

The method of synthesis follows procedures well known in the prior art. These procedures are determined by the type of reactants used to produce the desired structure. Common procedures for preparing sensitizing dyes of the type described herein are shown in *The Theory of the Photographic Process*, 4th Edit., Chapter 8, (1977), and in other references. The dye structures containing the sultone nucleus (I) of this invention are easily prepared and include the following: (Dyes II, III, V, and VII are merocyanine dyes, IV is an oxonol, and VI is a hemi-oxonol or styryl dye)

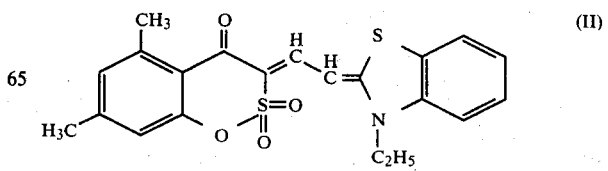

(II)

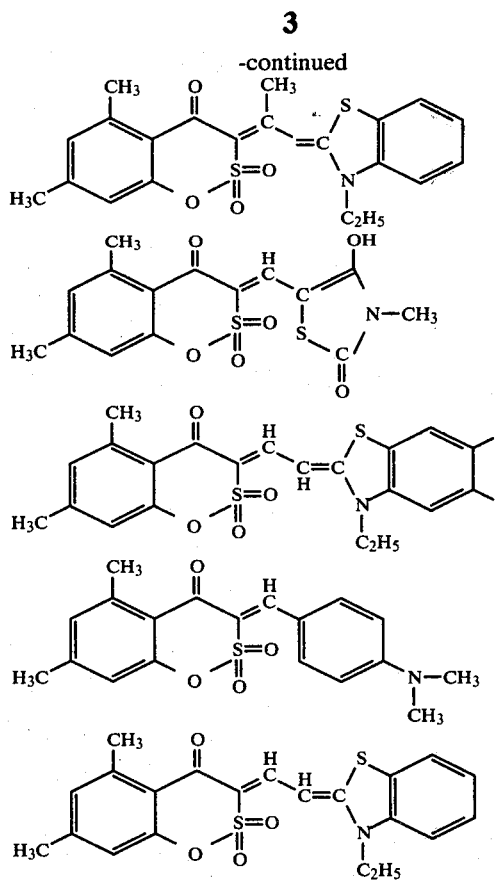

The sultone starting nucleus (I) of this invention can be conveniently prepared from 2-acetyl-3,5-dimethyl phenol (VIII) as follows:

A. 6 g (VIII) in 40 ml tetrahydrofuran solvent

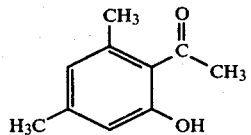

(THF) is reacted with thionyl chloride (SOCl₂, 10 ml in 15 ml THF) under nitrogen at room temperature for about 24 hours. The contents are poured into hexane to yield 3 g of 5,7-dimethyl-1,2-benzoxathian-4-one-2-oxide (IX)

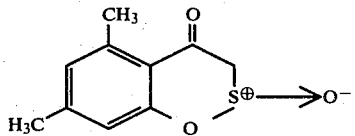

B. (I) can then be formed by oxidizing (IX) in acetic acid with hydrogen peroxide.

Synthesis of the dyes described above is shown in the following examples:

EXAMPLE 1

3-[(3-Ethyl-2-(3H)-benzothiazolylidene)ethylidene]-5,7-dimethylbenzoxathian-4-one-2,2-dioxide (structure II, above) is prepared as follows:

5,7-dimethylbenzoxathian-4-one-2,2-dioxide, 113 mg (0.5 mmoles) and 2-β-acetanilidovinyl-3-ethylbenzothiazolium iodide, 225 mg (0.5 mmoles) are heated to 70° C. in 5 ml absolute ethanol. Triethylamine (0.1 ml, 0.72 mmoles) is added and the mixture refluxed for 10 minutes, then cooled. The solid (160 mg) was collected and chromatographed on 10 g silica gel. Eluting with chloroform gave 106 mg (50%) dye mp 261°-262° C. λmax(EtOH) 487 nm, $\epsilon = 8.6 \times 10^4$ IR Spectrum: 1620 cm$^{-1}$, 1155 cm$^{-1}$ NMR (CDCl₃): δ8.3–6.5 (m, 8H, aromatic vinyl); 4.25 (m, 2H, CH₂ of Et); 2.7, 2.35 (two singlets, 3H each, aromatic methyls); 1.49 (t, 3H, CH₃ of Et).

Mass Spectrum: M⁺: 413.0764; Calc'd. for $C_{21}H_{19}NO_4S_2$: 413.0754.

EXAMPLE 2

3-[(3-Ethyl-2(3H)-benzothiazolylidene)isopropylidene]-5,7-dimethylbenzoxathian-4-one-2,2-dioxide (structure III, above) is prepared as follows:

5,7-dimethylbenzoxathian-4-one-2,2-dioxide, 70 mg (0.31 mmoles) and 2-(2-methoxypropenyl)-3-ethylbenzothiazolium ethosulfate, 103 mg (0.30 mmoles) are heated to 70° C. in absolute ethanol. Triethylamine, 0.1 ml (0.72 mmoles) is added and the resulting mixture refluxed for 10 minutes, then cooled. Water is added and the crude solid collected and chromatographed on 3 g silica gel. Eluting with chloroform gave 20 mg (15%) dye. mp 180° C. (d). λmax (EtOH) 487 nm.

IR Spectrum: 1675 cm$^{-1}$, 1600 cm$^{-1}$, 1150 cm$^{-1}$.

Mass Spectrum: M⁺: 427.0930; Calc'd for $C_{22}H_{21}NO_4S_2$: 427.0911.

EXAMPLE 3

3-Methyl-5-(5,7-dimethylbenzoxathian-4-one-2,2-dioxide-3-ylmethylene)-2-thiothiazolid-4-one (structuve IV, above) is prepared as follows:

5,7-dimethylbenzoxathian-4-one-2,2-dioxide, 2.0 g (8.9 mmoles) and 3-methyl-5-ethoxymethylenerhodanine, 2.0 g (9.9 mmoles) are heated to 70° C. in 70 ml of absolute ethanol. Triethylamine, 2.0 ml (14.4 mmoles) is added and the resulting mixture refluxed 5 minutes, then cooled. The mixture is acidified with 5% aqueous HCl, water added and the solid collected. This crude material is then dissolved in ethanol, made basic with triethylamine, and acidified with 5% aqueous HCl. Water and ethanol were added to bring the final solution to 2½ liters and 60:40 ethanol/water. The dye crystallized from this to give 1.87 g (54%) as the triethylammonium salt. mp 163°-165° C. λmax(EtOH) 475 nm, $\epsilon = 4.0 \times 10^4$ IR Spectrum: 1675 cm$^{-1}$, 1155 cm$^{-1}$.

NMR (d₆-DMSO): δ7.7 (s, 1H, vinyl); 6.97 (bs, 2H, aromatic); 3.37 (s, 4H, N—CH₃, OH); 3.07 (q, 6H, J=8 Hz, CH₂ of Et); 2.32 (s, 3H, aromatic CH₃); 1.17 (t, 9H, CH₃ of Et)

Mass Spectrum: M⁺: 382.9983; Calc'd. for $C_{15}H_{13}NO_5S_3$: 382.9955.

Analysis calc'd. for $C_{21}H_{28}N_2O_5S_3$: % C, 52.04 H, 5.82 N, 5.78 S, 19.85; Found: % C, 51.23 H, 5.76 N, 5.64 S, 20.02.

EXAMPLE 4

3-[3-Ethyl-5,6-methylenedioxy-2(3H)-benzothiazolylidene)ethylidene]-5,7-dimethylbenzoxathian-4-one-2,2-dioxide (structure V, above) is prepared as follows:

2-β-acetonilidovinyl-3-ethyl-5,6-methylenedioxybenzothiazolium iodide, 230 mg (0.49 mmoles) and 5,7- dimethylbenzoxathian-4-one-2,2-dioxide, 117 mg (0.52 mmoles) are heated to 70° C. in 5 ml of absolute ethanol. Triethylamine, 0.1 ml, (0.72 mmoles) is added and the resulting mixture refluxed for 10 minutes, then cooled. The solid is collected and chromatographed on 15 g silica gel. Eluting with chloroform gave 67 mg (36%) dye, mp 284°-288° C. (d). λmax (EtOH) 508 nm, $\epsilon = 6.3 \times 10^4$.

IR Spectrum: 1615 cm$^{-1}$, 1550 cm$^{-1}$, 1240 cm$^{-1}$, 1140 cm$^{-1}$

Mass Spectrum: M$^+$: 457.0680; Calc'd. for $C_{22}H_{19}NO_6S_2$: 457.0653

EXAMPLE 5

3-[4-dimethylaminobenzylidene]-5,7-dimethyl-1,2-benzoxathian-4-one-2,2-dioxide (structure VI, above) is prepared as follows:

5,7-Dimethyl-1,2-benzoxathian-4-one-2,2-dioxide, 232 mg (1 mmole) and p-dimethylaminobenzaldehyde, 114 mg (0.75 mmole) are heated to 70° C. in 5 ml of absolute ethanol. Piperidine, 0.1 ml (1 mmole) is added and the resulting mixture refluxed for 20 minutes, then cooled. The brilliant orange dye crystallized out to give 170 mg (63%) dye, mp 214°-217° C., λmax (CHCl$_3$) 460 nm, $\epsilon = 3.6 \times 10^4$.

IR Spectrum: 1620 cm$^{-1}$, 1130 cm$^{-1}$, 1170 cm$^{-1}$

NMR (CDCl$_3$): δ8.35 (s, 1H, vinyl); 7.95 (d, 2H, ½ A$_2$B$_2$; J=9 Hz, aromatic); 7.05 (bs, 2H, sultone aromatic); 6.8 (d, 2H, ½ A$_2$B$_2$; J=9 Hz, aromatic); 3.2 (s, 6H, N-methyls) 2.7 (s, 3H, aromatic methyl); 2.45 (s, 3H, aromatic methyl).

Mass Spectrum: M$^+$ 357.1024; Calc'd. for $C_{19}H_{19}NO_4S$ 357.1034.

Analysis calc'd. for $C_{19}H_{19}NO_4S$: % C, 63.84 H, 5.36 N, 3.92; Found: 63.65 H, 4.98 N, 4.16.

EXAMPLE 6

3-[(3-ethyl-2(3H)-benzoxazolylidene)ethylidene]-5,7-dimethylbenzoxathian-4-one-2,2-dioxide (structure VII, above) is prepared as follows:

5,7-Dimethylbenzoxathian-4-one-2,2-dioxide, 218 mg (0.965 mmoles) and 2-β-acetanilidovinyl-3-ethylbenzoxazolium iodide, 418 mg (0.965 mmoles) are heated to reflux. Triethylamine, 0.16 ml (1.15 mmoles) is added and the resulting mixture refluxed for 20 minutes, then cooled. The dye crystallized to give 263 mg (69%) orange crystals, mp>250° C., λmax (CHCl$_3$) 454 nm.

IR Spectrum: 1620 cm$^{-1}$, 1150 cm$^{-1}$.

NMR (CDCl$_3$): δ8.3 (d, J=14 Hz, 1H, vinyl); 7.3 (m, 5H, benzoxazole aromatic, vinyl); 6.9 (bs, 2H, benzoxathian aromatic); 4.0 (q, 2H, CH$_2$ of Et); 2.7, 2.3 (two singlets, 3H each, aromatic methyls); 1.4 (t, 3H, CH$_3$ of Et).

Mass Spectrum: M⊕: 397; Calc'd. for $C_{21}H_{19}NO_5S$: 397

EXAMPLE 7

A standard lithographic emulsion was prepared using inactive gelatin containing no chemical sensitizers such as sulfur or gold, and containing ca. 70 mole percent AgCl and ca. 30 mole percent AgBr. A sample comprising 140 g of this emulsion was mixed with 26 g of gelatin and 230 ml of distilled water and stirred for 10 minutes at 70° F. (about 21° C.) while the pH was adjusted to 6.0±0.1. The temperature was then raised to 95° F. (35° C.) for 10 minutes followed by an additional 10 minutes, at 110° F. (43.3° C.). At this point, 58 g of distilled water were added and the solution contained 14% calculated as silver bromide. Two portions of 100 g each were used in this example. The first sample (A, the control) was diluted with an equal volume of 7% aqueous gelatin and coated on a standard sample of photographic film base (polyethylene terephthalate containing both resin and a gelatin subbing layers) using a 6 mil knife. The second sample (B) was digested with 12 ml of Dye II in 1:1 acetone/ethanol (1 mg/ml) for 25 minutes at 120° F. (48.9° C.). This sample was diluted and coated like the control.

Wedge spectrograms were then made from each of the coatings following procedures outlined in the *SPSE Handbook of Photographic Science and Engineering*, Thomas, Jr., (Editor), John Wiley & Sons (Publ.), 1973, pages 822-825. Each exposed wedge spectrogram was developed in a standard mixed developer. White light speeds were determined from a sample exposed through a $\sqrt{2}$ step wedge with similar processing. Analysis of the results showed the following:

| Sample | White Light Speed | Spectral Sensitivity (nm) |
| --- | --- | --- |
| A-Control | 100 | 448 |
| B-Dye II | 158 | 543 |

There is no residual dye stain from the sample containing Dye II of this invention.

EXAMPLE 8

Example 7 was repeated using Dye IV in place of Dye II at 285 mg of dye per 1.5 moles of silver halide. The following results were obtained:

| Sample | White Light Speed | Spectral Sensitivity (nm) |
| --- | --- | --- |
| A-Control | 100 | 450 |
| B-Dye IV | 200 | 565 |

EXAMPLE 9

Using conditions similar to those described in Examples 7 and 8, Dye VII was tested and found to give adequate spectral sensitization of the emulsion out to about 500 nm and good white light speeds. Additionally, this dye was dischargeable with hydroxide ion and left no dye stain on the film processed as in Example 7.

Several other dye structures based on the sultone (I) were evaluated using Molecular Orbital (M.O.) calculations. This procedure is well known and is described in "The Theory of the Photographic Process", T. H. James (Editor), MacMillan Pub. Co., Inc., (4th Edit., 1977), pages 212 and 213. These calculations can be used to predict whether or not a particular structure will produce a photographic sensitizing dye. In all of the dyes tested for photographic sensitometry as in Example 7, specifically Dyes II, IV, VI, and VII, their sensitometry was found to match the predictions made by using M.O. calculations. The following additional structures have also been predicted to produce suitable sensitizing dyes based on M.O. calculations: (The last two are oxonols, and all the others are merocyanine dyes)

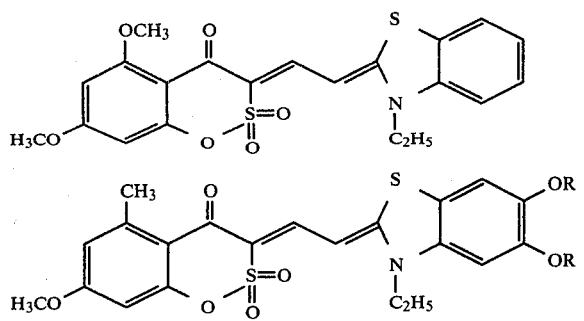 (X)
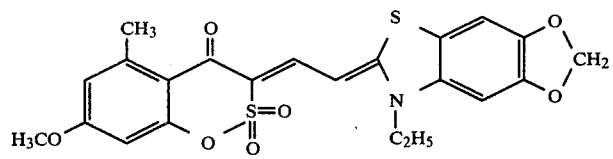 (XI)
R = C₁–C₃ alkyl
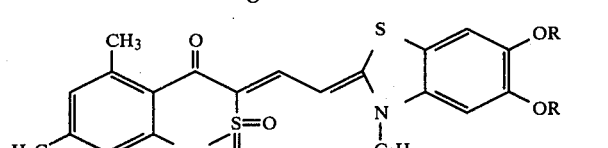 (XII)
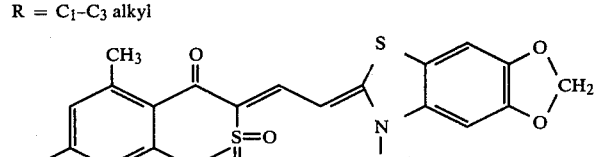 (XIII)
R = C₁–C₃ alkyl
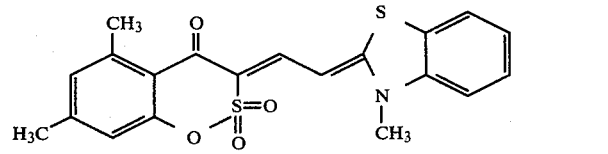 (XIV)
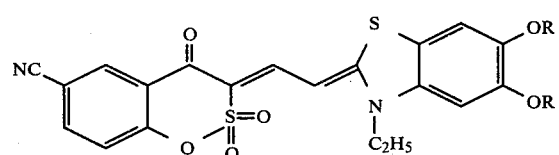 (XV)
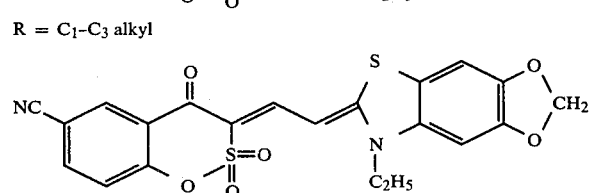 (XIV)
R = C₁–C₃ alkyl
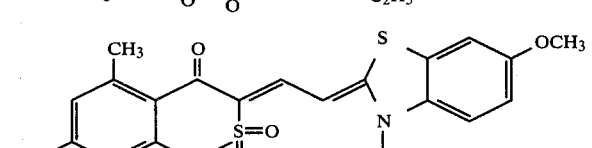 (XVII)
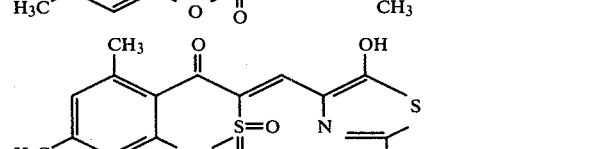 (XVIII)
 (XIX)
R = H, or C₁–C₃ alkyl

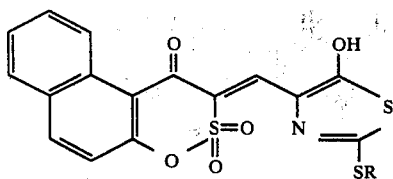

R = H, or $C_1$–$C_3$ alkyl (XX)

Dyes prepared from nucleus I can be used to extend the spectral response of any of the known silver halide emulsions, e.g., AgCl, AgBr, Ag bromochloride, and Ag iodobromide. Typically these are embodied in light-sensitive photographic elements comprising a light-sensitive gelatino-silver halide emulsion coated upon a support and containing one of the sensitizing dyes of this invention. These emulsions may be further sensitized with any number of other well-known sensitizers including gold and sulfur compounds as well as other optical sensitizers. The emulsions can also contain other adjuvants such as wetting agents, hardeners, antifoggants and the like and can be coated on any of the known photographic supports, such as paper and synthetic resin films; the preferred support is a poly(ethylene terephthalate) film of the type described in Alles, U.S. Pat. No. 2,779,684.

These novel dyes can be conveniently used and are easily dispersed in gelatin/silver halide emulsions using well-known techniques. These dyes are usually dissolved in water-miscible organic solvents such as the lower alcohols, acetone, or mixtures of these. In a preferred embodiment, these dye solutions are added to the silver halide emulsion in an amount of about 8 to 15 ml of dye solution per 100 g of 16% aqueous silver halide emulsion, wherein the dye solution contains about 1 mg of dye per 1 ml of solution.

The efficacy of this group of dyes is greatly enhanced by the lack of residual dye stain after the image is formed and processed.

BEST MODE

The oxonol dyes of structures IV and XIX represent the best mode.

I claim:

1. As a new composition of matter, a sensitizing or filter dye having one of the following general formulas:

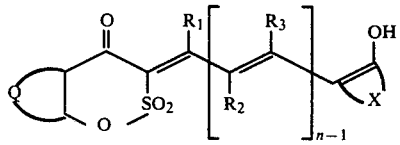
(A)

wherein Q represents sufficient carbon atoms to complete a benzo or naphto nucleus, or a substituted benzene or napthalene nucleus, $R_1$, $R_2$ and $R_3$ each represent H or a $C_1$–$C_3$ alkyl group, n=1, 2 or 3, and X represents sufficient nonmetallic atoms to complete a 5- or 6-membered heterocyclic or carbocyclic nucleus;

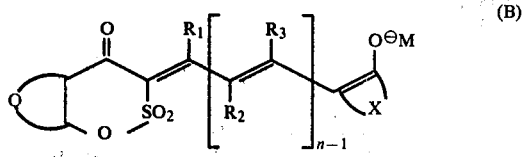
(B)

wherein Q, $R_1$, $R_2$, $R_3$ and n are the same as in formula A, and M is a mono-, di-, or trivalent metal;

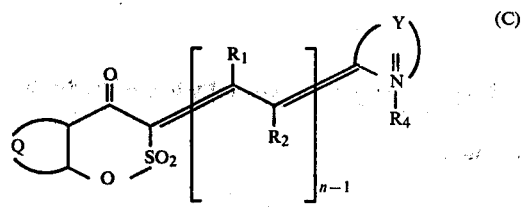
(C)

wherein Q, $R_1$, $R_2$ and n are the same as in formula A, $R_4$ is a $C_1$–$C_{12}$ alkyl, and Y represents sufficient nonmetallic atom to complete a 5- or 6-membered heterocyclic nucleus;

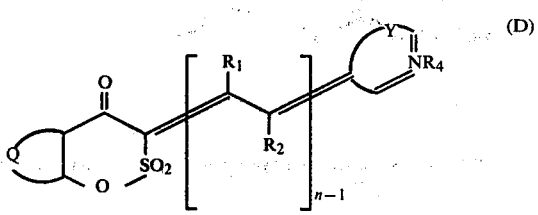
(D)

wherein Q, $R_1$, $R_2$, n, $R_4$, and Y are the same as in formula C; and

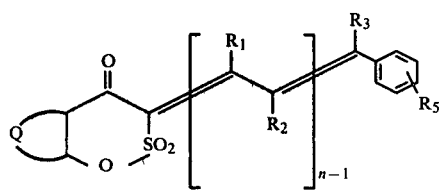
(E)

wherein Q, $R_1$, $R_2$, $R_3$ and n are the same as in formula A and $R_5$ can be H, a $C_1$–$C_{12}$ alkyl group, an $NO_2$ group, an alkyloxy or alkylthio group wherein the alkyl group contains 1–6 carbon atoms, or a dialkylamino group wherein each alkyl group contains 1–6 carbon atoms.

2. The composition of claim 1 wherein the dye has the formula

3. The composition of claim 1 wherein the dye has the formula

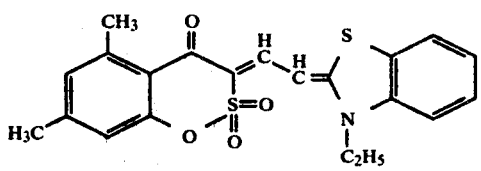

4. The composition of claim 1 wherein the dye has the formula

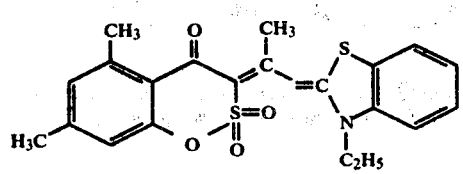

5. The composition of claim 1 wherein the dye has the formula

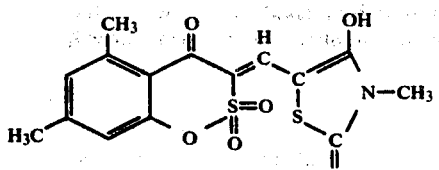

IV

6. The composition of claim 1 wherein the dye has the formula

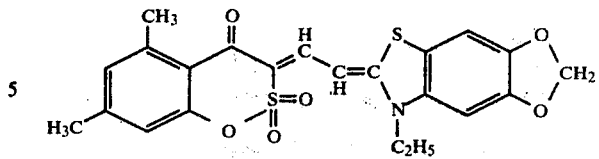

7. The composition of claim 1 wherein the dye has the formula

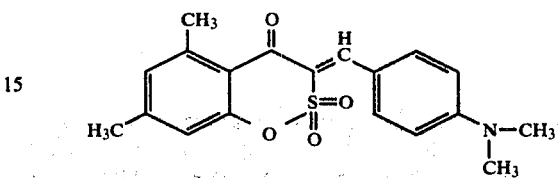

8. The composition of claim 1 wherein the dye has the formula

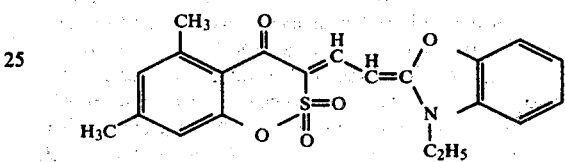

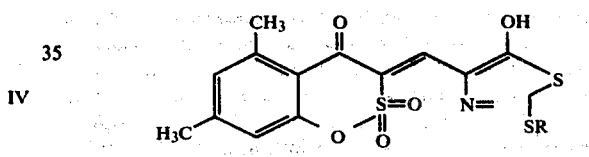

wherein R=H, or $C_1$–$C_3$ alkyl.

9. A light-sensitive photographic element comprising a support coated with a light-sensitive gelatino-silver halide emulsion containing the dye of claim 1.

10. A light-sensitive photographic element comprising a support coated with a light-sensitive gelatino-silver halide emulsion containing the dye of either claim 2, claim 3, claim 4, claim 5, claim 6, claim 7, or claim 8.

* * * * *